US008905759B2

(12) United States Patent
Gan et al.

(10) Patent No.: US 8,905,759 B2
(45) Date of Patent: Dec. 9, 2014

(54) SYSTEMS AND METHODS FOR DELIVERING SUBSTANCES INTO NANOPOROUS MINERALIZED TISSUES

(75) Inventors: Hiongyap Gan, Singapore (SG); Jongyoon Han, Bedford, MA (US); Frederico Barbosa de Sousa, Paraiba (BR)

(73) Assignees: Massachusetts Institute of Technology, Cambridge, MA (US); Universidade Federal de Paraiba, Joao Pessoa (BR)

( * ) Notice: Subject to any disclaimer, the term of this patent is extended or adjusted under 35 U.S.C. 154(b) by 0 days.

(21) Appl. No.: 13/492,090

(22) Filed: Jun. 8, 2012

(65) Prior Publication Data

US 2012/0315596 A1  Dec. 13, 2012

Related U.S. Application Data

(60) Provisional application No. 61/494,727, filed on Jun. 8, 2011.

(51) Int. Cl.
*A61C 5/00* (2006.01)
*A61C 19/06* (2006.01)
*A61N 1/05* (2006.01)
*A61N 1/30* (2006.01)

(52) U.S. Cl.
CPC ............ *A61C 19/066* (2013.01); *A61N 1/0548* (2013.01); *A61N 1/306* (2013.01)
USPC ............................................ 433/215; 604/20

(58) Field of Classification Search
CPC ....... A61Q 11/00; A61Q 3/02; A61C 19/066; A61C 19/063; A61C 17/005; A61C 17/227; A61C 19/06; A61C 3/00; A61C 5/062
USPC .......... 433/80, 215–216, 32; 606/10, 53–100, 606/246–331; 264/16–20; 427/2.26, 2.29; 424/49; 523/109, 120; 423/308; 607/50, 51; 174/70 R; 15/167.1; 624/16–20; 604/20

See application file for complete search history.

(56) References Cited

U.S. PATENT DOCUMENTS 5,051,401 A * 9/1991 Sikes ........................... 514/16.4
6,368,109 B2 * 4/2002 Lindquist ..................... 433/215

(Continued)

FOREIGN PATENT DOCUMENTS

WO     2008001388 A1    1/2008
WO     2008101256 A2    8/2008

OTHER PUBLICATIONS

Gan, H., et al., "Electrokinetic Transport in Dental Enamel", Enamel Conference (Jun. 8-12, 2011, Utica, Illinois).

*Primary Examiner* — Cris L Rodriguez
*Assistant Examiner* — Mirayda A Aponte
(74) *Attorney, Agent, or Firm* — Sutherland Asbill & Brennan LLP

(57) ABSTRACT

Methods and systems are provided for transporting a therapeutic or cosmetic substance into nanoporous mineralized tissue structures, such as teeth. The method may include contacting the nanoporous mineralized tissue structure with an ionic solution including the therapeutic or cosmetic substance; and simultaneously applying to the nanoporous mineralized tissue structure an electrical potential effective to transport the therapeutic or cosmetic substance into the nanopores of the nanoporous mineralized tissue structure. The system may include at least one pair of electrodes which includes a first electrode configured for contacting the nanoporous mineralized tissue structure and a second electrode; and a power source and control circuitry for generating an electrical potential between the first electrode and the second electrode effective to transport a therapeutic or cosmetic substance, in an ionic solution in contact with a surface of the nanoporous mineralized tissue structure, into the nanopores of the nanoporous mineralized tissue structure.

23 Claims, 6 Drawing Sheets

(56) References Cited

U.S. PATENT DOCUMENTS

| | | | |
|---|---|---|---|
| 6,641,396 B2* | 11/2003 | Pasquantonio et al. | 433/217.1 |
| 7,775,795 B2* | 8/2010 | Khawaled et al. | 433/32 |
| 7,985,072 B2* | 7/2011 | Belikov et al. | 433/215 |
| 2002/0055085 A1* | 5/2002 | Perdomini | 433/224 |
| 2006/0223032 A1* | 10/2006 | Fried et al. | 433/215 |
| 2008/0199830 A1* | 8/2008 | Fontenot et al. | 433/215 |
| 2009/0117513 A1* | 5/2009 | Nemeh et al. | 433/32 |
| 2010/0047742 A1* | 2/2010 | Pitcock et al. | 433/215 |
| 2010/0303925 A1* | 12/2010 | Pitts et al. | 424/602 |

* cited by examiner $t = 0$ s and $V_{app} = 0$ V $t = 350$ s and $V_{app} = 50$ V $t = 1100$ s and $V_{app} = 50$ V $t = 2000$ s and $V_{app} = 50$ V content continues …

SYSTEMS AND METHODS FOR DELIVERING SUBSTANCES INTO NANOPOROUS MINERALIZED TISSUES

CROSS-REFERENCE TO RELATED APPLICATIONS

This application claims benefit of U.S. Provisional Application No. 61/494,727 filed Jun. 8, 2011, the disclosure of which is incorporated herein by reference.

BACKGROUND

The present disclosure is generally in the field of systems, devices, and methods for actively delivering beneficial substances into nanoporous mineralized tissue structures, such as teeth.

Dental enamel is composed primarily of calcium hydroxyapatite, and its anatomical structure is nanoporous. Transport processes in dental enamel take place mainly by diffusion, the rate of which is directly proportional to pore sizes in the enamel. Typically, the pores may contain water that may be replaced by substances through diffusion. The transport of substances through dental enamel nanopores and dentin micro and nanopores may be important for tissue formation, pathogenesis, and for preventive, therapeutic, and cosmetic procedures in dentistry.

Methods are well known for topically applying substances, such as fluorinating or whitening agents or other substances to the surface of teeth. Unfortunately, however, these topical treatments rely on passive diffusion of the substances into the tooth and are highly inefficient. Even with electrochemical (redox reaction) processes, such as disclosed in U.S. Pat. No. 7,775,795 to Khawaled et al., the techniques essentially provide only a surface treatment, which would penetrate generally no more than 2 to 5 microns into the tooth surface. Accordingly, there remains a need to provide systems and methods for delivering beneficial substances deeper into the nanoporous structure of the tooth, thereby providing better or more efficient dental treatments.

It would also be desirable to provide methods and systems for quantifying or comparing the rate of delivery of beneficial substances into teeth or other nanoporous mineralized tissue structures.

SUMMARY

In one aspect, methods are provided for transporting a therapeutic or cosmetic substance into a nanoporous mineralized tissue structure. In an embodiment, the method includes contacting the nanoporous mineralized tissue structure with an ionic solution comprising the therapeutic or cosmetic substance and simultaneously applying to the nanoporous mineralized tissue structure an electrical potential effective to transport the therapeutic or cosmetic substance into the nanopores of the nanoporous mineralized tissue structure. The method can be carried out on a nanoporous mineralized tissue structure in vitro or in viva.

In another aspect, methods are provided for measuring the transport of a substance of interest into a nanoporous mineralized tissue structure. In an embodiment, the method includes contacting the nanoporous mineralized tissue structure with an ionic solution comprising the substance of interest; applying to the nanoporous mineralized tissue structure in contact with the ionic solution an electrical potential effective to transport the substance of interest into the nanopores of the nanoporous mineralized tissue structure; and measuring an electrical current associated with the applied electrical potential as a function of time. The change in measured electrical current can be used to determine the rate of penetration of the substance of interest into the nanoporous mineralized tissue structure.

In yet another aspect, systems, devices, and kits are provided for delivering a therapeutic or cosmetic substance into a nanoporous mineralized tissue structure. In an embodiment, the system includes (i) at least one pair of electrodes comprising a first electrode and a second electrode, with at least the first electrode being configured for contacting the nanoporous mineralized tissue structure; (ii) a power source and control circuitry for generating an electrical potential between the first electrode and the second electrode effective to transport a therapeutic or cosmetic substance, in an ionic solution in contact with a surface of the nanoporous mineralized tissue structure, into the nanopores of the nanoporous mineralized tissue structure. In an embodiment, a kit is provided that includes a system for transporting a therapeutic or cosmetic substance into a nanoporous mineralized tissue structure and an ionic solution comprising a therapeutic or cosmetic substance for delivery into a nanoporous mineralized tissue.

Additional aspects will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The present disclosure may be better understood with reference to the following figures. Corresponding reference numerals designate corresponding parts throughout the figures, and components in the figures are not necessarily to scale.

Figure 6A:
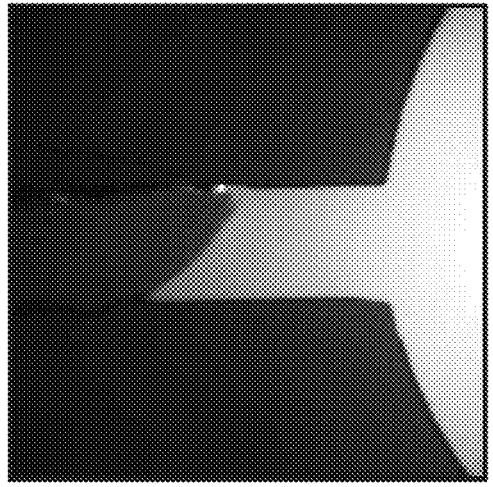
FIG. 6A is a CCD camera photographic image showing a fluorescence signal before application of an electrical potential (50V DC) to a microfluidics device including a dental enamel specimen.
Figure 6B:
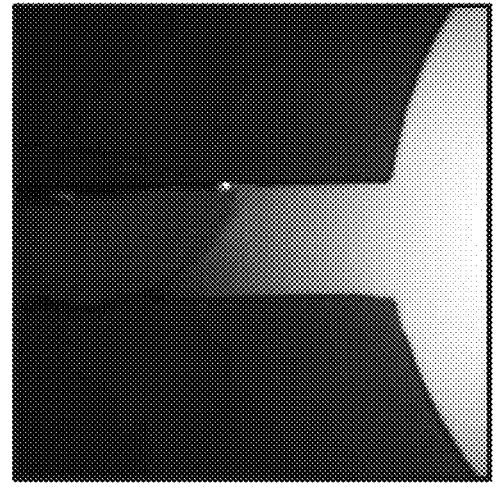
FIG. 6B is a CCD camera photographic image showing the depletion of a fluorescence signal at a time interval of 350 seconds after application of the electrical potential (50V DC) to the microfluidics device including a dental enamel specimen.
Figure 6C:
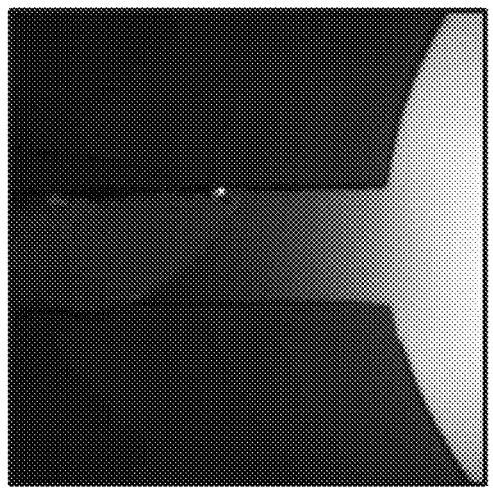
FIG. 6C is a CCD camera photographic image showing depletion of a fluorescence signal at a time interval of 1100 seconds after application of the electrical potential (50V DC) to the microfluidics device including a dental enamel specimen.
Figure 6D:
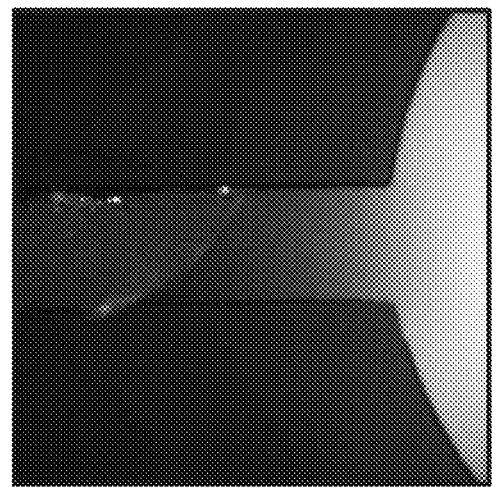

FIG. 6D is a CCD camera photographic image showing depletion of a fluorescence signal at a time interval of 2000 seconds after application of the electrical potential (50V DC) to the microfluidics device including a dental enamel specimen.

Figure 7:
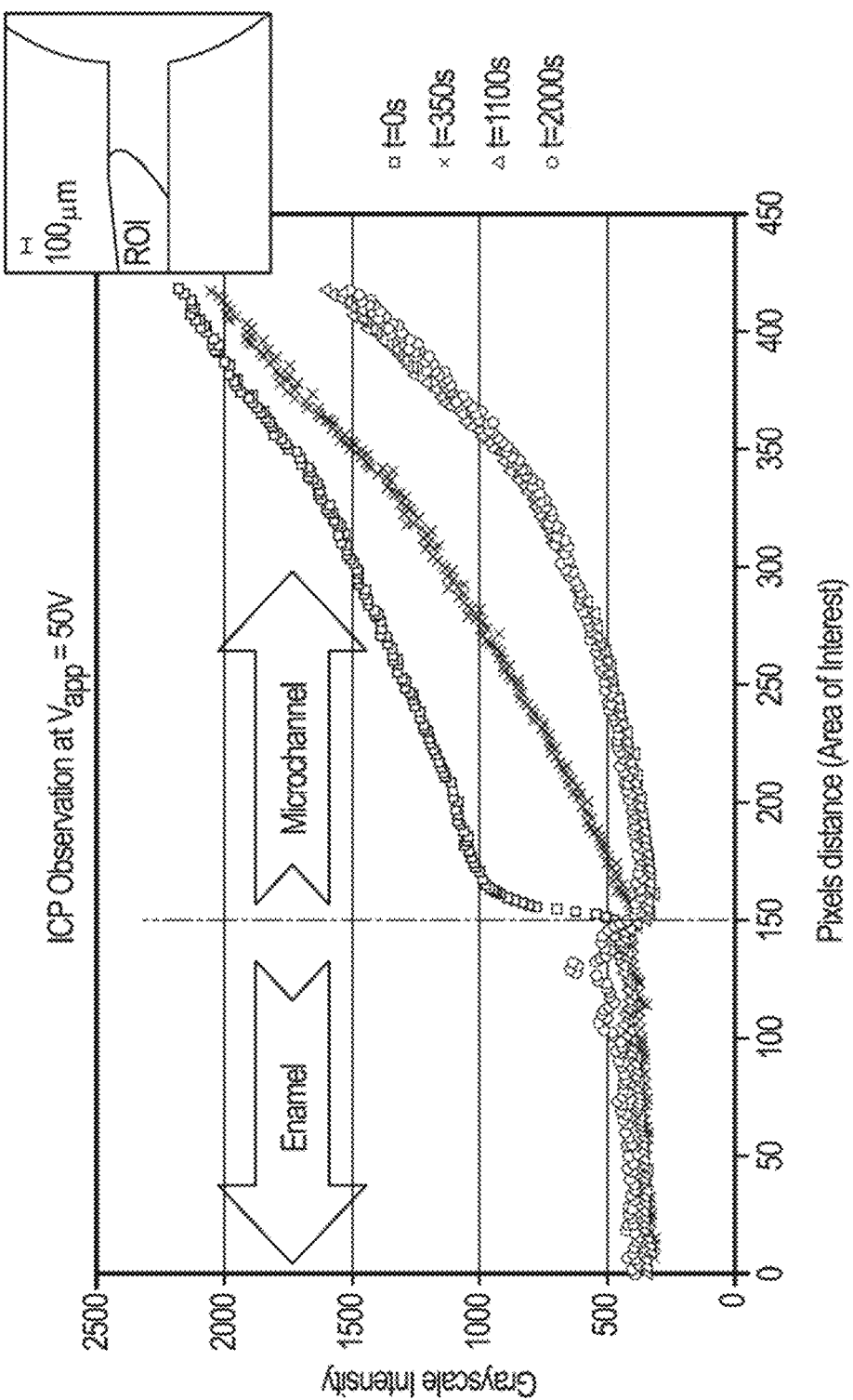

FIG. 7 is a graph showing grayscale intensity at different time points during application of a DC voltage in a microfluidics device including a dental enamel specimen.

Figure 8:
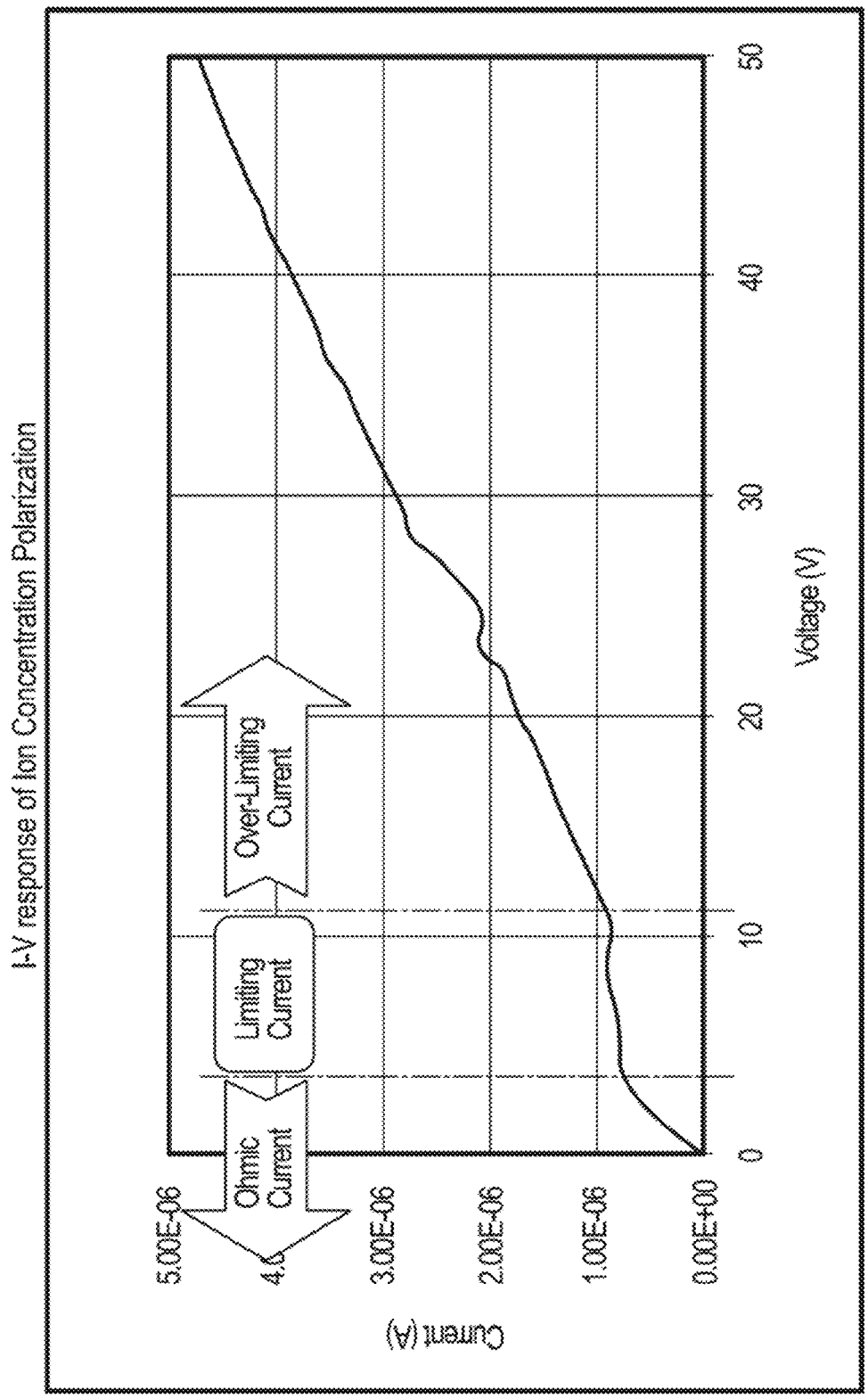

FIG. 8 is a graph showing a sweep response of electrical current vs. applied potential as observed for a dental enamel specimen.

DETAILED DESCRIPTION

Methods and systems have been developed for using electric potential gradient-driven fluid flow as a means for controlling fluid transport in nanoporous mineralized tissue structure. The term "nanoporous mineralized tissue structure" as used herein includes, but is not limited to, tooth or bone, or a particular part or parts thereof, such as the enamel, dentin, cementum, and/or cartilage. The nanoporous mineralized tissue structure may be located within or excised from human or other mammalian subjects. With this electrokinetic fluid flow, therapeutic and cosmetic substances advantageously can be driven and controllably delivered into the pores and channels of tooth enamel and dentin, for example.

Without being bound by any single theory, it is submitted that under typical in vivo conditions, many of the nanopores of mineralized tissues may be filled with an aqueous ionic liquid such as saliva, which contains water. The presently disclosed systems and methods enable the electrokinetically replacement of at least a portion of the water content of nanoporous mineralized tissue structures, thereby accelerating the migration of water from the nanopores and accelerating the migration of ionic solutions comprising therapeutic or cosmetic substances, or other agents of interest, into the nanopores. The transported substance need not be ionic but should be solubilized in the ionic solution.

Electrokinetic Method for Substance Delivery

In one embodiment, the method for transporting a therapeutic or cosmetic substance into a nanoporous mineralized tissue structure includes contacting the nanoporous mineralized tissue structure with an ionic solution which contains the therapeutic or cosmetic substance and applying an electrical potential to the nanoporous mineralized tissue structure in a manner such that the therapeutic or cosmetic substance is transported electrokinetically from the ionic solution and into the nanopores of the nanoporous mineralized tissue structure. The method may be applied to nanoporous mineralized tissue structures in vivo or in vitro.

As used herein, the term "therapeutic or cosmetic substance" includes, but is not limited to, whitening agents, mineralizing agents, remineralizing agents, resins, pigmented resins, fluorinating agents, and drugs. In some embodiments, the ionic solution may include more than one therapeutic or cosmetic substance. The ionic solution may be an aqueous solution comprising water and a water soluble, ionizable form of the therapeutic or cosmetic substance.

In a particular embodiment, the electrokinetically driven therapeutic or cosmetic substance is transported to a depth of at least 500 microns into the nanopores of the nanoporous mineralized tissue structure. In another embodiment, the therapeutic or cosmetic substance is transported to a depth of at least 350 microns into the nanopores of the nanoporous mineralized tissue structure. In still another embodiment, the therapeutic or cosmetic substance may be transported to a depth of at least 200 microns into the nanopores of the nanoporous mineralized tissue structure. In an embodiment, the therapeutic or cosmetic substance is transported to a depth of from about 200 microns to about 500 microns into the nanopores of the nanoporous mineralized tissue structure.

The primary factors that determine the efficacy of the electrokinetic transport process include the placement of the electrodes on a nanoporous mineralized tissue structure, the magnitude of the applied electrical potential, and the duration of the applied electrical potential. The application of the electrical potential to the nanoporous mineralized tissue structure generally includes the selective positioning of electrodes in and/or around the tissue structure (or at least a portion the tissue structure) such that the path of electrokinetic transport is into and/or through the nanopores of the tissue structure. In one embodiment, the method includes contacting a first electrode to a first portion of the nanoporous mineralized tissue structure and positioning a second electrode of opposite polarity at or near a second portion of the nanoporous mineralized tissue. Then, an electrical potential can be generated between the first and second electrodes. The pair of electrodes includes an anode and a cathode. The electrical potential may be generated using essentially any source of DC electric power, such as a battery or capacitor. In some embodiments, the applied electrical potential may be from about 0.001 V to about 12 V, from about 0.01 V to about 10 V, or from about 0.1 V to about 1 V. In some embodiments, an effective treatment can be accomplished with an applied for a treatment time from a few minutes to about 3 hours, to about 2 hours, to about 1 hour, or to about 30 minutes. In embodiments, the treatment may include application of electrical potential from 0.001 V to 12 V for between 3 minutes and 3 hours.

Figure 1:
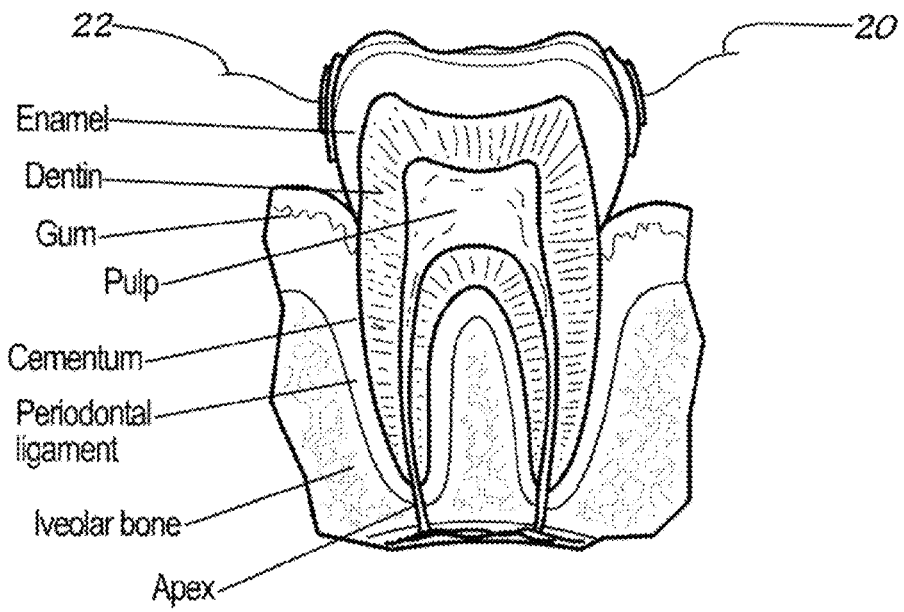
FIG. 1 is a cross-sectional view of a pair of electrodes contacting a tooth in accordance with an embodiment of the present invention.

In an embodiment, the nanoporous mineralized tissue structure includes a tooth or teeth. In a particular embodiments, the first electrode and the second electrode are in contact with the nanoporous mineralized tissue structure on exterior surfaces of the structure. As illustrated by FIG. 1, the first electrode 20 contacts a first portion (e.g., an exterior surface) of the enamel of the tooth, and the second electrode 22 contacts a second, in this case opposed, portion (also an exterior surface) of the enamel of the tooth. The first electrode 20 may be the cathode, and the second electrode 22 may be the anode. The pair of electrodes 20, 22 are detachably attached to the enamel surface, for example using a biocompatible adhesive material, such as a photo-curing or self-adhering gel. Such biocompatible gels are known in the art. Alternatively, the electrodes may be temporarily mechanically secured (e.g., clamped) in contact with the enamel of the tooth. Suitable fasteners are known in the art or can be readily adaptable from those known in the art.

Figure 2:
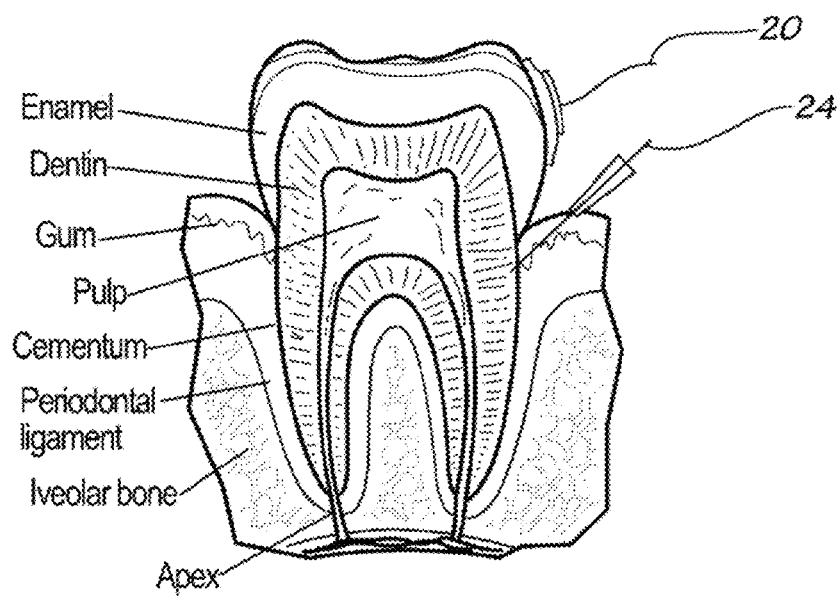
FIG. 2 is a cross-sectional view of a pair of electrodes contacting a tooth in accordance with another embodiment of the present invention.

Another embodiment of an electrode pair for electrokinetically transporting a substance into a tooth is shown in FIG. 2. Here, the first electrode 20 is located as shown in FIG. 1; however, the second electrode 24 is in the form of a needle or microneedle that penetrates into the gingiva and periodontal ligament (non-invasive) or the dentin (invasive) of a tooth. The first electrode 20 may be the cathode, and the second electrode 24 may be the anode. In both of the embodiments shown in FIGS. 1 and 2, an electric potential is generated between the electrodes, which are positioned such that the fluid electrokinetically induces flow path is into and out of the nanoporous structure of the tooth.

In yet another embodiment (not shown), the first electrode is placed into contact with the interior wall of a dental cavity, and the second electrode is placed into contact with a second portion of the tooth such as the enamel or dentin at a site away from the placement of the first electrode. In this embodiment, the first electrode may be in the form of a needle-shaped electrode dimensioned to fit into the dental cavity.

The methods described herein may be used to delivery a variety of therapeutic or cosmetic substances for dental applications. In one embodiment, the therapeutic or cosmetic substance includes a dental whitening agent. For example, the whitening agent may comprise a bleaching agent, including but not limited to hydrogen peroxide and carbamide peroxide. In another example, the whitening agent may comprise 2-hydroxyethylmethacrylate dental resin. In another example, the whitening agent may comprise a pigmented fluid resin with pigmented nanoparticles.

In one embodiment, the therapeutic or cosmetic substance may be a prophylactic agent. For instance, the prophylactic agent may be a composition useful for the mitigation or prevention of dental caries. It may, for example; include a fluoride-containing compound.

In another embodiment, the therapeutic or cosmetic substance comprises a restorative agent. For example, the restorative agent may comprise a saturated solution of hydroxyapatite. As another example, the restorative agent may include a fluoride-containing compound. In still other case, the restorative agent may include a restorative dental resin.

In yet another embodiment, the therapeutic or cosmetic substance comprises a fluid resin that may be used to increase the adhesion force between a natural tissue and a dental prosthetic. Without being limited to any single theory, electrokinetic transportation of the fluid resin into the nanopores of a dental tissue may provide increased surface contact area between the resin and the dental tissues, thereby enhancing the adhesion between the dental tissue and the dental prosthetic.

In another embodiment, the therapeutic or cosmetic substance may comprise a fluid resin, hydroxyapatite solution, or other fluid material suitable for application to bone tissue. For example, a fluid resin, such as a titanium-containing resin, may be used to enhance repair of bone fractures, by electrokinetic delivery into the nanopores or channels of bone tissue.

In a particular embodiment, the therapeutic or cosmetic substance comprises a drug. Examples of drugs include antibiotic agents and growth factors, including but not limited to (1) hyaluronic acid; (2) amelogenin, an enamel protein that may be synthesized in vitro and is known to induce repair of soft connective tissue, dental pulp, cementum, periodontal ligament and bone and to stimulate osteointegration with titanium implants; (3) bone morphogenetic protein, a protein with biological effects similar to amelogenin; and (4) antibiotics, such as gentamicin and flucloxacilin, applied to bone tissue, considering the widely known difficulties in treating infections in compact bone and that are a common cause of bone necrosis. Other suitable drugs are known in the art.

Measuring the Electrokinetic Transport of a Substance

In another aspect, the methods and systems described herein can be used to measuring the transport of a substance of interest (e.g., a therapeutic or cosmetic substance) into a nanoporous mineralized tissue structure. The measurement procedure may be applied in vitro on samples of intact or sectioned nanoporous mineralized tissue structures, such as enamel and dentin in teeth. This may be useful, for example, in developing a particular therapeutic or cosmetic treatment composition and/or procedure. It may be useful in testing various ionic solutions comprising a therapeutic or cosmetic substance in order develop/optimize a formulation for use in electrokinetic transport as described above.

In one embodiment, the method includes contacting the nanoporous mineralized tissue structure with an ionic solution comprising the substance of interest; applying an electrical potential to the nanoporous mineralized tissue structure in contact with the ionic solution; and measuring an electrical current, associated with the applied electrical potential, as a function of time. The rate of transport of the substance of interest into the nanopores of the nanoporous mineralized tissue structure may be determined based at least in part on the electrical current measurement obtained as a function of time. In another embodiment, birefringence of a nanoporous mineralized tissue structure is measured, and changes in birefringence as a function of electrokinetic delivery of a substance of interest into the nanoporous mineralized tissue structure may be measured. For example, the change in birefringence of dental enamel may be determined as a function of electrokinetic delivery of a therapeutic or cosmetic agent.

Systems and Kits for Electrokinetic Transport of a Substance

In another aspect, a system is provided for transporting a substance, such as a therapeutic or cosmetic substance, into a nanoporous mineralized tissue structure. The system includes at least a pair of electrodes (an anode and a cathode) and control circuitry and a power source for generating an electrical potential between the electrodes that is effective to transport a therapeutic or cosmetic substance, contained in an ionic solution that is in contact with a surface of the nanoporous mineralized tissue structure, into the nanopores of the nanoporous mineralized tissue structure. The power source and control circuitry may be include digital or analog components, hardware, software, and wiring known in the art, which can control the application of a DC voltage or current to the electrodes.

The pair of electrode may comprise a first electrode and a second electrode, where at least the first electrode is configured for contacting the nanoporous mineralized tissue structure. In certain embodiments, the pair of electrodes is configured for contacting a tooth of a patient in vivo. In one embodiment, the first electrode includes a pad of photo-curing dental resin or an adhesive gel for detachably securing the first electrode to an exterior surface of a tooth, as illustrated in FIG. 1. In another embodiment, the second electrode includes a needle or microneedle that is configured for insertion into the dentin or deeper enamel of the tooth or into the gum surrounding the tooth, as illustrated in FIG. 2. The needle or microneedle may be formed of a biocompatible, electrically conductive material, such stainless steel or other metals.

Figure 4:
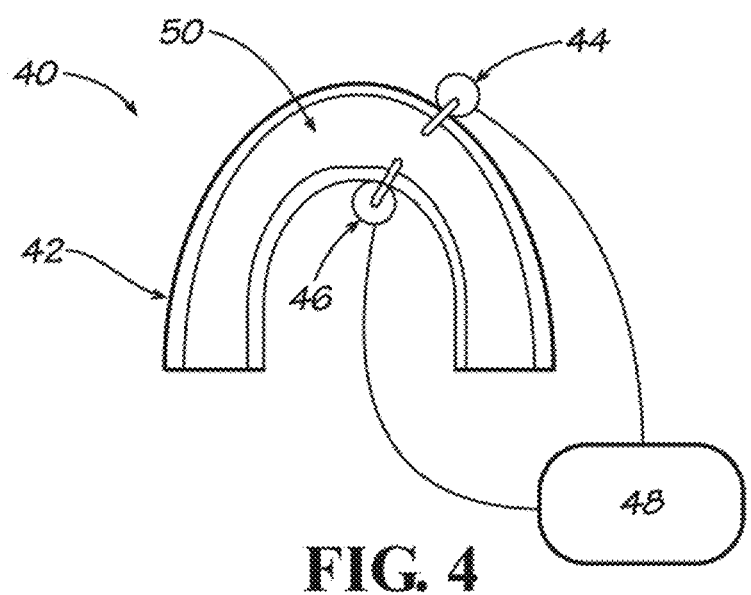
FIG. 4 is a schematic diagram of a system for in vivo electrokinetic transport of a substance into a tooth in accordance with an embodiment of the present invention.

The system may further include a fluid containment device for holding the ionic solution in a contacting relationship with the nanoporous mineralized tissue while the electrical potential is generated between the first and second electrodes. In one embodiment, the fluid containment device may comprise a dental tray, which includes at least one wall structure forming a channel for receiving the teeth of a patient. FIG. 4 illustrates treatment system 40 which includes dental tray 42 and power source/control circuitry 48. The dental tray 42 includes first electrode 44 and second electrode 46 which are disposed in the channel 50 of the dental tray 42, in a position to contact the enamel and or dentin of a tooth as described above, which a subject bites into the tray with his or her teeth placed into the channel. Only a single pair of electrodes is shown, but additional electrodes may be included in the tray to contact other of the subject's teeth. In an embodiment, the channel includes an array of electrodes corresponding to each tooth in the channel. The channel would contain an ionic solution of a therapeutic or cosmetic agent, added to the dental tray before or after the subject's teeth are positioned into the channel in contact with the electrodes.

The system may used to electrokinetically deliver a variety of therapeutic or cosmetic substances to one or more teeth of a subject. Examples of such substances include whitening agents, restorative agents, mineralizing agents, remineralizing agents, resins, pigmented resins, fluorinating agents, drugs, and combinations thereof. The system may be used to delivery a single substance or to deliver multiple substances simultaneously or in series.

To avoid spilling and to keep a sufficient quantity of the ionic solution within the channel during the treatment process, the channel may be provided with an elastic, porous matrix (e.g., a sponge) to hold the ionic solution, or in another embodiment, the ionic solution may be provided in a viscous liquid or gel form.

In another aspect, a kit of parts is provided for transporting a therapeutic or cosmetic substance into a nanoporous mineralized tissue structure. In one embodiment, the kit includes the systems described above and at least one container of an ionic solution comprising a therapeutic or cosmetic substance for delivery into a nanoporous mineralized tissue structure. The kit may include multiple containers of the same or different ionic solutions comprising therapeutic or cosmetic substances. In another embodiment, the kit may further include a dental tray or other device for holding the ionic solution in a contacting relationship with the nanoporous mineralized tissue while the electrical potential is generated between the first and second electrodes. In some embodiments, the therapeutic or cosmetic substance may be selected from the group consisting of whitening agents, restorative agents, drugs, and combinations thereof.

The systems and methods described above will be further understood with reference to the following non-limiting examples.

EXAMPLE 1

Microfluidic Testing Platform for Measuring Transport Performance

In a working example, the transport performance was evaluated by quantifying optical birefringence and real-time electric current response.

Procedure:

Thin ground sections (2×0.5×0.1 mm) of normal enamel from human erupted permanent third molars were prepared and inserted into a polydimethylsiloxane-based microfluidic device to conduct electrokinetic flow experiments. Test solutions of low ionic strength (1, 10, and 100 mM KCl) and high ionic strength (Thoulet's solution with a refractive index of 1.56) were tested on four samples of the ground tooth enamel.

Prior to the experiment, the ground sections of enamel were placed into a microfluidic device and the enamel was exposed to deionized water for 24 hours, resulting in the nanopores of the enamel being saturated with deionized water.

Figure 3:
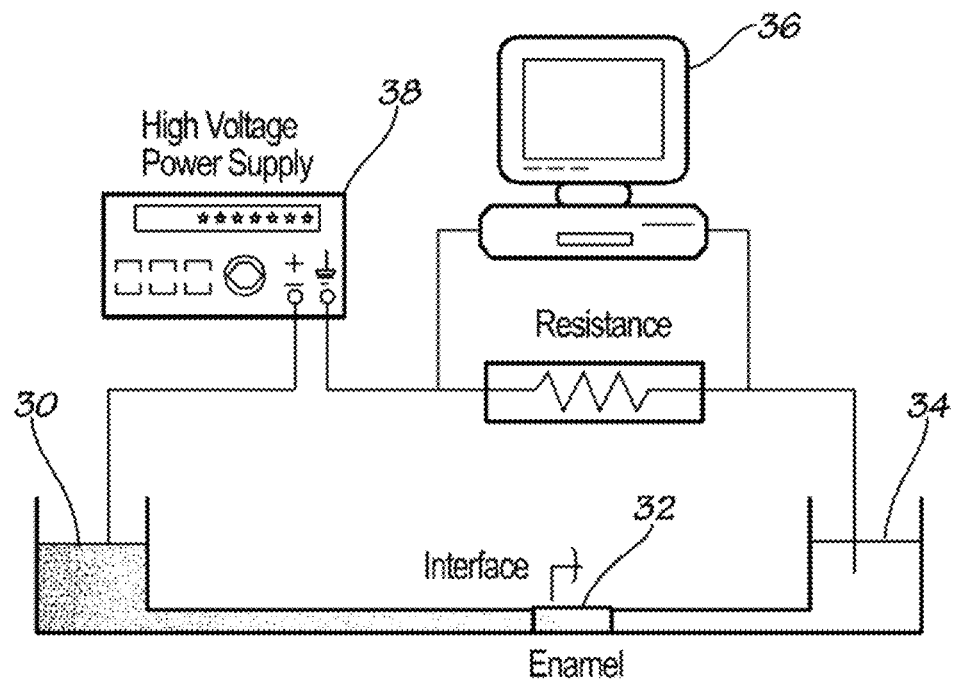
FIG. 3 is a schematic diagram of an exemplary electrical current monitoring setup in accordance with an embodiment of the present invention.

To begin the experiment, and as illustrated in FIG. 3, the test solutions were filled into a first microreservoir 30 and deionized water was filled into a second microreservoir 34. Both microreservoirs 30, 34 were connected to the microfluidic device 32 that contained the ground tooth enamel. An electrical potential ($V_{app}$=1.0 V) was applied from the power source 38 and the contents of microreservoir 30 were gradually pumped into the microfluidic device 32, thereby displacing the deionized water from the enamel contained in the microfluidic device 32. As the ionic liquid flowed into the microfluidic device 32, the system conductivity was altered, and hence the electrical current through the whole system was changed. These changes were monitored, over a period of time, using a microcomputer 36. When the ionic liquid from the first microreservoir 30 completely displaced the deionized water from the enamel contained in the microfluidic device 32, a constant electrical current was reached.

Figure 5:
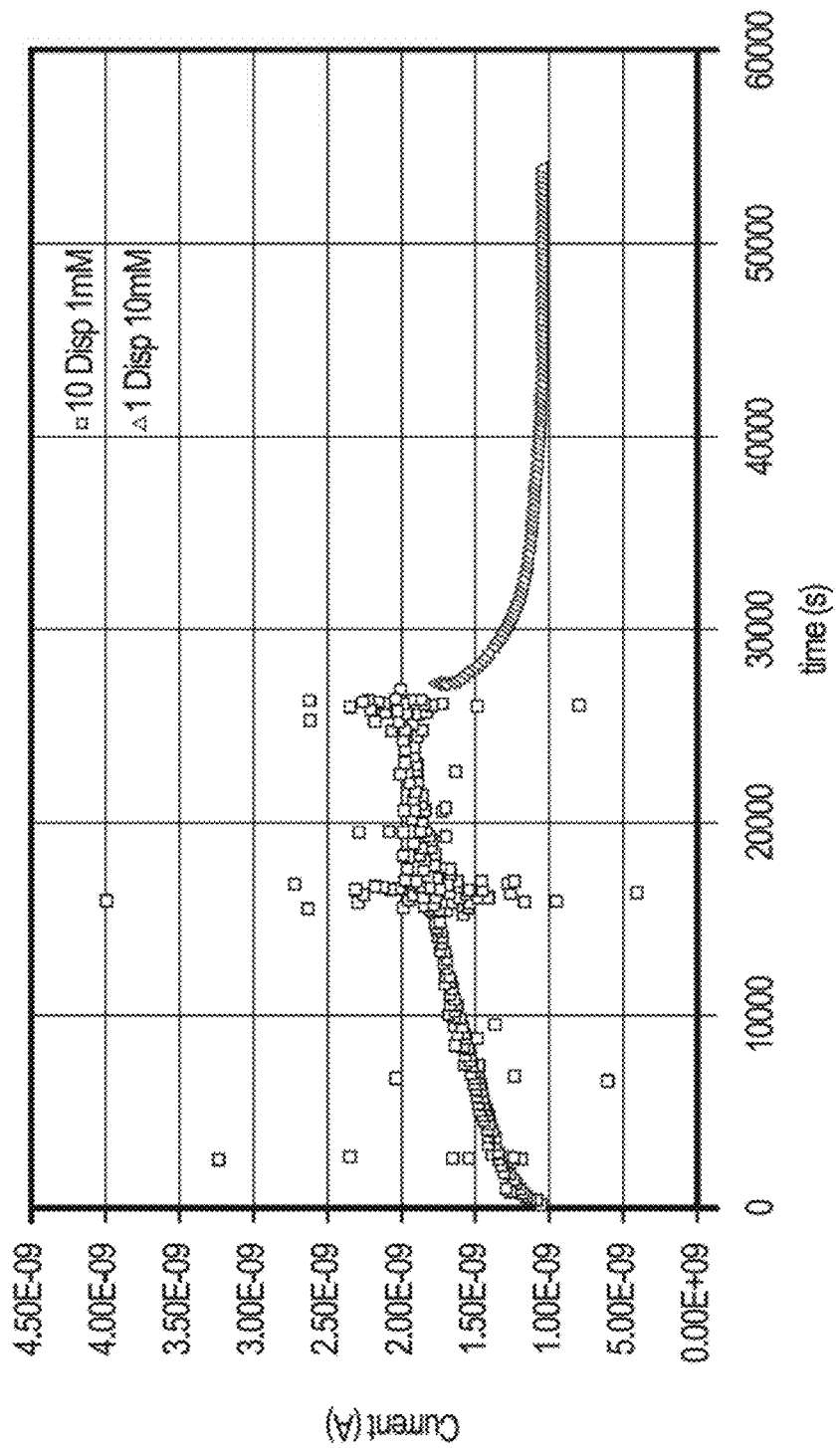
FIG. 5 is a graph showing the change in electrical current over time, performed at a constant electrical potential, in accordance with an embodiment of the present invention.

Results:

For the low ionic strength solutions, effective transport of the ions into the enamel was enhanced by the electrical driving force. The apparent or phenomenological mobility of ions, $D_{app}$, was measured as $2.6 \times 10^{-8}$ cm$^2$/s (compared to apparent diffusion coefficient, $D_{app}$ of $2 \times 10^{-10}$ cm$^2$/s, as measured by natural diffusion characterization methods). FIG. 5 illustrates the observed change in current as a function of time for 1 mM KCl and 10 mM KCl solutions.

In the electrical current monitoring method, real-time electrical current response of the displacement flow process was monitored while the liquid initially filling the enamel was electrokinetically displaced by another liquid with a different ionic concentration. During the electrokinetic pumping, the higher concentration ionic solution diffused into the nanopores of the enamel and displaced an equal volume of the lower concentration electrolyte out of the nanopores. As a consequence, the total resistance of the liquid in the enamel sample changed and the current increased, as is shown in FIG. 5. Once the lower concentration solution in the enamel sample was completely replaced by the higher concentration solution, the current reached a constant maximum value. The time for the current to reach the plateau value was the time required to complete the filling of the nanopores via the electrokinetic pumping and thus can be related to the average velocity via, $$U_{ave} = L/\Delta t \quad (1)$$

Where L is the total length of the channel and $U_{ace}$ is the average velocity.

The current monitoring technique offered a simple method for measuring the apparent mobility. The major drawback inherent with this technique, especially when considering a heterogeneous and tortuosity flow path through the nanopores, was the difficulty in determining the exact time required for a complete displacement process. Therefore, the average electrokinetic velocity in a microchannel was then evaluated by using the slope of the current-time relationship. Thus, a more accurate estimate of the average velocity was obtained. The slope of the current response curve was given by $$gradient_{I-t} \Delta I/\Delta t \quad (2)$$

Where $\Delta I$ and $\Delta t$ are the changes in current and time over the linear range.

In electrokinetic flow, the total current consists of three components: the bulk conductivity current, $I_{condbulk}$, the surface concentration current, $I_{condsurf}$, and the convection current $I_{conv}$. Since the convection current is several of orders of magnitude smaller than the other two current components, it can be ignored. Then, under an applied electrical field, $E_x$, the total current can be shown as $$I_{total} = I_{cond.\ bulk} + I_{cond.\ surf} = \lambda_b A_c E_x + \lambda_s L E_x \quad (3)$$

Substituting equation 6 for the difference of the current where $\Delta\lambda_s = 0$, equation 3 can be rewritten as $$gradient_{I-t} = \frac{\Delta I}{\Delta t} = \frac{A_c E_x \Delta \lambda}{\Delta t} = U_{ave} \frac{A_c E_x \Delta \lambda}{L}, \quad (4)$$

where $\Delta\lambda=\lambda_2-\lambda_1$ is the difference in bulk conductivity between the high and the low concentration solutions.

It is known that when an ionic solution moving through a microscale or even smaller flow channel is acted upon by a uniform electric field, it will be accelerated until it reaches a constant drift velocity according to the formula, $$U_{ave}=\mu_{eo}E_x \qquad (5)$$

By substituting equations 4 and 5 into the Nernst-Einstein equation, the $\mu_{eo}$ can be expressed as $$\mu_{eo} = \frac{\lambda}{zF} = \frac{U_{ave}}{E_x} = \frac{gradient_{I,t}L}{A_c\Delta\lambda(E_x)^2} \qquad (6)$$

Sample Calculation for Displacement Flow Experiment in FIG. 5

The initial input values were, L=1.257 mm, $E_x$=666.667 V/m, $\Delta\lambda$=0.12 S/m, $\lambda_1$=7.6×10$^{-10}$ Å. From FIG. 3, the gradient was estimated as 2.05×10$^{-14}$ Å/s. From equation 6, $\mu_{eo}$ was calculated as 5.19×10$^{-12}$ m/Vs. By equation 5, the average velocity was 4.13×10$^{-9}$ m/s. Hence, the effective diffusion coefficient was estimated as 2.6×10$^{-8}$ cm$^2$/s.

Birefringence Measurement

Additionally, a full replacement of the water volume in the ground enamel samples was observed when Thoulet's solution was used, based on a plateau of birefringence values of −0.005 (−5×10$^{-3}$) after 3 hours of treatment.

Measurements were performed at a point located in the center of the area with the highest birefringence.

Retardance (mean of 5 measurements)=508.7 nm
Sample thickness=90000 nm
Signal of birefringence=negative
Observed birefringence (BRobs)=508.7/90000=−0.005574

The enamel BRobs was given by:

$$BR_{obs} = \frac{V_1V_2(n_1^2-n_2^2)^2}{2(V_1n_1+V_2n_2)\cdot[(1+V_1)n_2^2+V_2n_1^2]} - 0.0065\cdot A\cdot V_1$$

where the first term in the right hand side is the form birefringence (BRform), related to the non-mineral content, and the second term in the right hand side is the intrinsic birefringence (BRint), related to the mineral content. $V_1$ and $V_2$ are the mineral and non-mineral volume fractions, respectively. A is a factor for alignment of the crystallites (0.85). $n_1$ (1.62) and $n_2$ are the refractive indexes of the mineral and non-mineral phases, respectively. The higher the "$n_1-n_2$" difference, the higher the BRform. Thus, $n_2$ is given by:

$$n_2 = 1.33\frac{\alpha_1}{V_2} + n_i\frac{\alpha_2}{V_2} + 1.56\frac{\beta}{V_2}$$

where $\alpha_1$ and $\alpha_2$ are the firmly and loosely bound water volume fractions, respectively. $\beta$ is the organic volume fraction and $n_i$ is the refractive index of the immersion medium in the case when it replaces part of the water volume only. For a full replacement of water by the immersion medium, $n_i$ multiplies both $\alpha_1$ and $\alpha_2$.

For a site in dental enamel with a mineral volume of 93% (the mean value for normal enamel), the predicted birefringence after immersion in Thoulet's 1.56 considering full replacement of all the water volumes ($\alpha_1$ and $\alpha_2$) is −0.004988. The predicted range for normal enamel (mineral volume ranging from 88 to 98%) is −0.0049 to −0.0057. Thus, the experimental BRobs in Thoulet's 1.56 after EOF was within the predicted range.

Additionally, a high BRobs was obtained from a dental enamel sample with a high refractive index aqueous solution after a short period of time (~3 hours).

EXAMPLE 2

Ion Concentration Polarization Generated in Dental Enamel

Nanofluidic channels with critical dimensions of 10~100 nm exhibit unique permselectivity to ions due to effects from their overlapping electrical double layer. Application of a direct current across such a channel can initiate ion concentration polarization (ICP) near the nanofluidic structures by generating strong concentration gradients of ionic species through a permselective ion current. Once this concentration polarization is triggered, the concentrations of both cations and anions decrease on the anodic side of the junction (ion depletion) and increase on the cathodic side (ion enrichment). A good understanding of this phenomenon may be important to electrokinetic-based tooth treatment applications, in particular to optimize the efficiency of ion transport in dental enamel.

In this working example, ICP in dental enamel material was experimentally observed by fluorescence concentration measurements and by an electrical current vs. applied potential sweep response plot. This set of observations showed that ICP was observed on dental enamel specimens, showing a possible mode for amplified electroosmotic pumping that could be employed in designing ion transportation for enamel and other nanoporous mineralized tissue structures.

Procedure:

Enamel specimens (~1.5 mm×300 μm×100 μm) were prepared and inserted into a polydimethylsiloxane-based microfluidic device for ICP observations. A test solution of 5 mM KCl with AlexFluor 488 fluorescein (5 μL of 1.55 mg/L fluorescein in 5 mL of KCl solution) was added to the microfluidic device. In a first experiment, an electric potential (DC, 50 V) was applied to observe the electrokinetic injection of fluorescein into the dental enamel under ICP conditions. In a second experiment, an electric potential (DC, 0-50 V) was applied to a dental enamel specimen and a sweep response plot of electrical current (I) vs. potential (V) was recorded.

Results:

As illustrated in FIGS. 6A-6D, CCD camera images of the fluorescence depletion at different time intervals was observed. In FIG. 6A, at t=0 s and with no external applied potential, only a slight or negligible fluorescence was observed in the enamel specimen due to natural diffusion during loading of the test solution, while most of the fluorescence signal was observed in the microchannel of the microfluidic device. In FIG. 6C, at t=1100 s and with $V_{app}$=50 V, depletion of the fluorescence signal was clearly observed at the vicinity of enamel (microchannel) indicating the generation of ICP. Finally, at t=2000 s (FIG. 6D), although the fluorescence depletion was maintained, a slight penetration of fluorescence was observed across the migration path of the enamel specimen. These figures show that fluorescence was depleted at the anodic side of the enamel which ICP was generated. The ICP region expanded outwardly toward the bulk reservoir with time because more cations were accumulated at the entrance region and repelled the incoming cations.

The grayscale intensity of the depletion process at different time intervals is illustrated in FIG. 7. The Y-axis represents the instant fluorescence intensity and the x-axis represents the line of interest (yellow line shown in the small picture in the corner of the graph). The grayscale intensity plots shows the changes of intensity at that yellow line over time. As shown, the ICP was correlated to the depletion of fluorescence intensity as was observed at the entrance of the enamel specimen. This implied that the dental enamel was negatively charged and the overlapping of electrical double layers that was induced on the walls of the nanopores created an environment that demonstrated permselectivity to ions. The figure thus shows that fluorescein was injected electrokinetically even under over-limiting current regime. The observations showed that a unique mode for amplified electroosmotic pumping could be identified to obtain the optimum transportation of ions.

The electrical current (I) vs. potential (V) sweep response plot, measuring the observed electrical current (I) over a range of electrical potentials (0-50 V) applied to a dental enamel specimen, is illustrated in FIG. 8. The curve of the sweep response plot was typical for what has been observed for other nanofluidic channel materials undergoing ICP, confirming that ICP was observed on the dental enamel specimen. Three distinct regions were depicted in the plot, including the ohmic current, limiting current, and over-limiting current regions. The results indicated that the dental enamel specimen was negatively charged and the overlapping of electrical double layers induced on the walls of the nanopores created permselectivity to ions. This observation was in good agreement with the literature (Teaford, Mark F. et al "Development, Function and Evolution of Teeth," Cambridge Univ. Press, 2000).

It should be apparent that the foregoing relates only to the preferred embodiments of the present invention and that numerous changes and modifications may be made herein without departing from the spirit and the scope of the invention as defined by the following claims and equivalents thereof.

We claim:

1. A method for transporting a therapeutic or cosmetic substance into a nanoporous mineralized tissue structure, comprising:
    contacting the nanoporous mineralized tissue structure with an ionic solution comprising the therapeutic or cosmetic substance; and simultaneously
    applying to the nanoporous mineralized tissue structure an electrical potential in a manner effective to electrokinetically transport the therapeutic or cosmetic substance into the nanopores of the nanoporous mineralized tissue structure,
    wherein the application of the electrical potential comprises contacting a first electrode to a first portion of the nanoporous mineralized tissue structure and contacting a second electrode to a second portion of the nanoporous mineralized tissue structure, and generating an electrical potential between the first and second electrodes.

2. The method of claim 1, wherein the first portion comprises a first exterior surface of the nanoporous mineralized tissue structure.

3. The method of claim 2, wherein the second portion comprises a second exterior surface of the nanoporous mineralized tissue structure.

4. The method of claim 2, wherein the second portion comprises an interior region of the nanoporous mineralized tissue structure.

5. The method of claim 1, wherein the therapeutic or cosmetic substance is transported at least 500 microns into the nanopores of the nanoporous mineralized tissue structure.

6. The method of claim 1, wherein the nanoporous mineralized tissue structure comprises at least one tooth.

7. The method of claim 6, wherein the therapeutic or cosmetic substance comprises a whitening agent.

8. The method of claim 6, wherein the therapeutic or cosmetic substance comprises a restorative agent.

9. The method of claim 1, wherein the application of the electrical potential comprises contacting a first electrode to a wall of a cavity in a tooth and contacting a second electrode onto an outer surface of the tooth.

10. The method of claim 1, wherein the therapeutic or cosmetic substance comprises a drug.

11. A method for measuring the transport of a substance of interest into a nanoporous mineralized tissue structure, comprising:
    contacting the nanoporous mineralized tissue structure with an ionic solution comprising the substance of interest;
    applying to the nanoporous mineralized tissue structure, which is in contact with the ionic solution, an electrical potential in a manner effective to electrokinetically transport the substance of interest into the nanopores of the nanoporous mineralized tissue structure; and
    measuring an electrical current associated with the applied electrical potential as a function of time,
    wherein the application of the electrical potential comprises contacting a first electrode to a first portion of the nanoporous mineralized tissue structure and contacting a second electrode to a second portion of the nanoporous mineralized tissue structure, and generating an electrical potential between the first and second electrodes.

12. The method of claim 11, further comprising determining a rate of transport of the substance of interest into the nanopores of the nanoporous mineralized tissue structure based at least in part on the electrical current measurement.

13. The method of claim 11, wherein the nanoporous mineralized tissue structure comprises a tooth enamel.

14. The method of claim 13, further comprising measuring the change in birefringence of the tooth enamel.

15. A system for transporting a therapeutic or cosmetic substance into a nanoporous mineralized tissue structure, comprising:
    at least one pair of electrodes comprising a first electrode and a second electrode, at least the first electrode being configured for contacting the nanoporous mineralized tissue structure; and
    a power source and control circuitry for generating an electrical potential between the first electrode and the second electrode in a manner effective to electrokinetically transport a therapeutic or cosmetic substance, in an ionic solution in contact with a surface of the nanoporous mineralized tissue structure, into the nanopores of the nanoporous mineralized tissue structure,
    wherein the at least one pair of electrodes is configured for contacting a tooth in vivo.

16. The system of claim 15, further comprising a fluid containment device for holding the ionic solution in a contacting relationship with the nanoporous mineralized tissue while the electrical potential is generated between the first and second electrodes.

17. The system of claim 16, wherein the fluid containment device comprises a dental tray which includes at least one wall structure forming a channel for receiving the teeth of a patient.

18. The system of claim 15, wherein the therapeutic or cosmetic substance is selected from the group consisting of whitening agents, restorative agents, drugs, and combinations thereof.

19. The system of claim 15, wherein the first electrode comprises a pad of photo-curing dental resin or adhesive gel for detachably securing the first electrode to an exterior surface of the tooth.

20. The system of claim 15, wherein the second electrode comprises a needle or microneedle, wherein the needle or microneedle is configured for insertion into the dentin or deeper enamel of the tooth or into the gum surrounding the tooth.

21. A kit of parts comprising:
the system of claim 15; and
an ionic solution comprising a therapeutic or cosmetic substance for delivery into a nanoporous mineralized tissue structure.

22. The kit of claim 21, wherein the therapeutic or cosmetic substance is selected from the group consisting of whitening agents, restorative agents, drugs, and combinations thereof.

23. A method for transporting a therapeutic or cosmetic substance into a nanoporous mineralized tissue structure, comprising:
contacting a first electrode to a first portion of a nanoporous mineralized tissue structure having nanopores filled with an aqueous liquid comprising water;
contacting a second electrode to a second portion of the nanoporous mineralized tissue structure;
contacting the nanoporous mineralized tissue structure with an ionic solution comprising water and a non-ionic therapeutic or cosmetic substance; and simultaneously
generating an electrical potential between the first and second electrodes to form a path of electrokinetic transport into and/or through nanopores of the nanoporous mineralized tissue structure,
thereby electrokinetically replacing at least a portion of the water in the nanopores with the ionic solution.

* * * * *